US008683881B2

(12) United States Patent
Bouasaysy et al.

(10) Patent No.: US 8,683,881 B2
(45) Date of Patent: Apr. 1, 2014

(54) INTRAGASTRIC SPACE FILLERS AND METHODS OF MANUFACTURING INCLUDING IN VITRO TESTING

(75) Inventors: Outhit Bouasaysy, Corona, CA (US); Mark Ashby, Laguna Niguel, CA (US)

(73) Assignee: ReShape Medical, Inc., San Clemente, CA (US)

( * ) Notice: Subject to any disclaimer, the term of this patent is extended or adjusted under 35 U.S.C. 154(b) by 716 days.

(21) Appl. No.: 12/753,751

(22) Filed: Apr. 2, 2010

(65) Prior Publication Data

US 2010/0251837 A1    Oct. 7, 2010

Related U.S. Application Data

(60) Provisional application No. 61/166,675, filed on Apr. 3, 2009.

(51) Int. Cl.
*G01N 17/00* (2006.01)
(52) U.S. Cl.
USPC .......................................................... 73/865.6
(58) Field of Classification Search
USPC .......................................................... 73/866.4
See application file for complete search history.

(56) References Cited

U.S. PATENT DOCUMENTS

| | | |
|---|---|---|
| 2,493,326 A | 1/1950 | Trinder |
| 4,133,315 A | 1/1979 | Berman et al. |
| 4,246,893 A | 1/1981 | Berson |
| 4,356,824 A | 11/1982 | Vazquez |
| 4,416,267 A | 11/1983 | Garren et al. |
| 4,485,805 A | 12/1984 | Foster, Jr. |
| 4,598,699 A | 7/1986 | Garren et al. |
| 4,694,827 A | 9/1987 | Weiner et al. |
| 4,723,547 A | 2/1988 | Kullas et al. |
| 4,899,747 A | 2/1990 | Garren et al. |
| 5,084,061 A | 1/1992 | Gau et al. |
| 5,123,840 A | 6/1992 | Nates |
| 5,259,399 A | 11/1993 | Brown |
| 5,263,934 A | 11/1993 | van den Haak |
| 5,273,536 A | 12/1993 | Savas |
| 5,318,530 A | 6/1994 | Nelson, Jr. |

(Continued)

FOREIGN PATENT DOCUMENTS

| | | |
|---|---|---|
| DE | 8708978 U1 | 11/1987 |
| EP | 0 457 456 | 5/1990 |

(Continued)

OTHER PUBLICATIONS

International Search Report; International Application No. PCT/US2010/050260; Applicant: ReShape Medical, Inc., Mailing Date: Jun. 17, 2011, 9 pages.

(Continued)

*Primary Examiner* — R. A. Smith
*Assistant Examiner* — Alex Devito
(74) *Attorney, Agent, or Firm* — Perkins Coie LLP

(57) ABSTRACT

An in vitro testing process for simulating conditions of a stomach, comprising, in combination: providing an intragastric device to an acetone bath; inducing swelling of the intragastric device; exacerbating weak spots in the intragastric device; observing the results; and estimating the results of an in vivo study. Improvements to an intragastric space filler to reduce failure at a balloon to shaft area including an adhesive fillet, washers, a balloon cuff and collar, a molded in balloon fillet, and a one-piece molded balloon assembly.

10 Claims, 14 Drawing Sheets

(56) References Cited

U.S. PATENT DOCUMENTS

Figure 1:
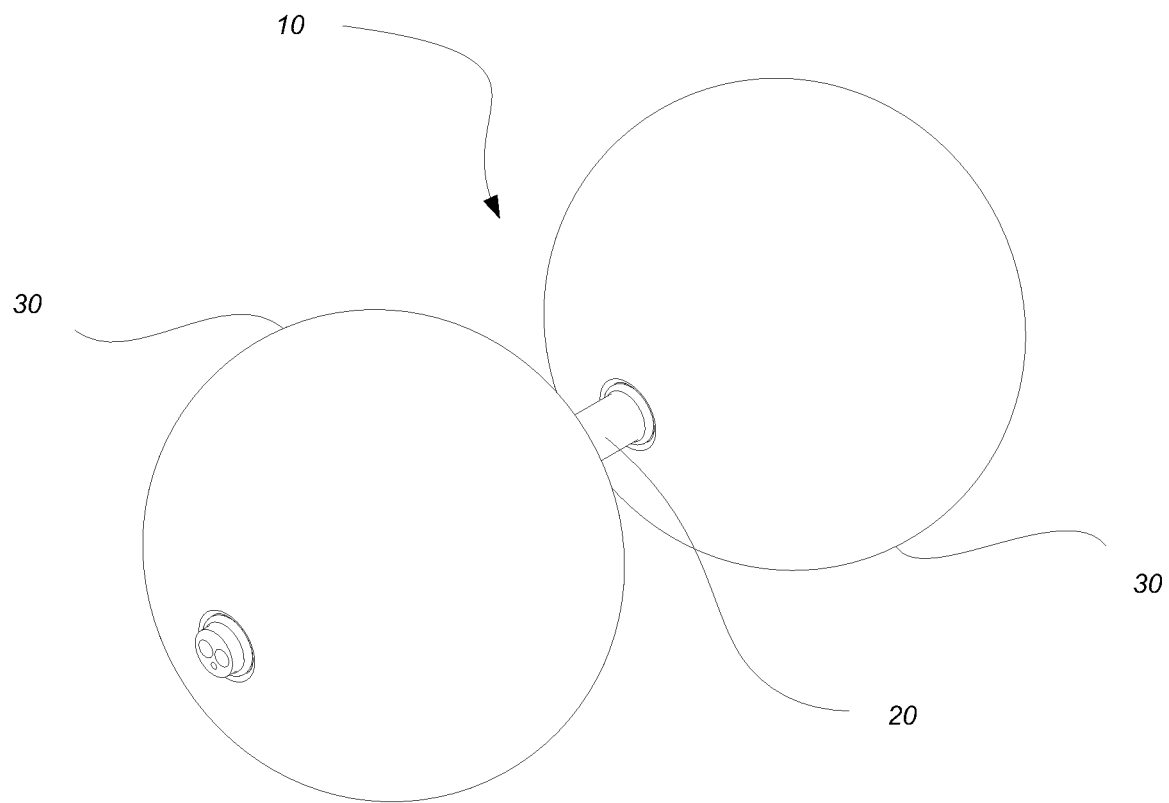

| | | |
|---|---|---|
| 5,334,187 A | 8/1994 | Fischell et al. |
| 5,431,173 A | 7/1995 | Chin et al. |
| 5,496,271 A | 3/1996 | Burton et al. |
| 5,575,772 A | 11/1996 | Lennox |
| 5,643,209 A | 7/1997 | Fugoso et al. |
| 5,730,722 A | 3/1998 | Wilk |
| 5,779,728 A | 7/1998 | Lunsford et al. |
| 5,857,991 A | 1/1999 | Grothoff et al. |
| 5,876,376 A | 3/1999 | Schwab et al. |
| 5,938,669 A | 8/1999 | Klaiber et al. |
| 5,993,473 A | 11/1999 | Chan |
| 6,149,621 A | 11/2000 | Makihara |
| 6,254,355 B1 | 7/2001 | Gharib |
| 6,276,567 B1 | 8/2001 | Diaz et al. |
| 6,280,411 B1 | 8/2001 | Lennox |
| 6,423,058 B1 | 7/2002 | Edwards et al. |
| 6,454,785 B2 | 9/2002 | De Hoyos Garza |
| 6,535,764 B2 | 3/2003 | Imran et al. |
| 6,547,788 B1 | 4/2003 | Maguire et al. |
| 6,579,301 B1 | 6/2003 | Bales et al. |
| 6,613,018 B2 | 9/2003 | Bagga et al. |
| 6,613,037 B2 | 9/2003 | Khosravi et al. |
| 6,706,010 B1 | 3/2004 | Miki et al. |
| 6,746,460 B2 | 6/2004 | Gannoe et al. |
| 6,826,428 B1 | 11/2004 | Chen et al. |
| 6,850,128 B2 | 2/2005 | Park |
| 6,866,657 B2 | 3/2005 | Shchervinsky |
| 6,869,431 B2 | 3/2005 | Maguire et al. |
| 6,890,300 B2 | 5/2005 | Lloyd et al. |
| 6,890,346 B2 | 5/2005 | Ganz et al. |
| 6,923,754 B2 | 8/2005 | Lubock |
| 6,939,299 B1 | 9/2005 | Petersen et al. |
| 6,958,052 B1 | 10/2005 | Charlton |
| 7,001,419 B2 | 2/2006 | DiCaprio et al. |
| 7,016,735 B2 | 3/2006 | Imran et al. |
| 7,020,531 B1 | 3/2006 | Colliou et al. |
| 7,033,373 B2 | 4/2006 | de la Torre et al. |
| 7,056,305 B2 | 6/2006 | Garza Alvarez |
| 7,076,305 B2 | 7/2006 | Imran et al. |
| 7,131,945 B2 | 11/2006 | Fink et al. |
| 7,483,746 B2 | 1/2009 | Lee et al. |
| 7,828,749 B2 | 11/2010 | Douglas et al. |
| 2001/0022988 A1 | 9/2001 | Schwarz et al. |
| 2001/0037127 A1 | 11/2001 | De Hoyos Garza |
| 2002/0055757 A1 | 5/2002 | Torre |
| 2002/0107515 A1 | 8/2002 | Edwards et al. |
| 2002/0161388 A1 | 10/2002 | Samuels et al. |
| 2002/0173804 A1 | 11/2002 | Rousseau |
| 2003/0114878 A1 | 6/2003 | Diederich et al. |
| 2003/0171768 A1 | 9/2003 | McGhan |
| 2003/0187390 A1 | 10/2003 | Bates et al. |
| 2004/0044354 A1 | 3/2004 | Gannoe et al. |
| 2004/0059289 A1 | 3/2004 | Garza Alvarez |
| 2004/0059290 A1 | 3/2004 | Palasis |
| 2004/0087902 A1 | 5/2004 | Richter |
| 2004/0106899 A1 | 6/2004 | McMichael et al. |
| 2004/0116897 A1 | 6/2004 | Aboul-Hosn |
| 2004/0127915 A1 | 7/2004 | Fleenor et al. |
| 2004/0186502 A1 | 9/2004 | Sampson |
| 2004/0220665 A1* | 11/2004 | Hossainy et al. ............ 623/1.42 |
| 2004/0236280 A1 | 11/2004 | Rice et al. |
| 2004/0236361 A1 | 11/2004 | Sakurai |
| 2004/0254600 A1 | 12/2004 | Zarbatany et al. |
| 2005/0027283 A1 | 2/2005 | Richard et al. |
| 2005/0027313 A1 | 2/2005 | Shaker |
| 2005/0038415 A1 | 2/2005 | Rohr et al. |
| 2005/0055039 A1 | 3/2005 | Burnett et al. |
| 2005/0059990 A1 | 3/2005 | Ayala et al. |
| 2005/0075624 A1 | 4/2005 | Miesel |
| 2005/0085792 A1 | 4/2005 | Gershowitz |
| 2005/0119674 A1 | 6/2005 | Gingras |
| 2005/0143784 A1 | 6/2005 | Imran |
| 2005/0159769 A1 | 7/2005 | Alverdy |
| 2005/0177103 A1 | 8/2005 | Hunter et al. |
| 2005/0192615 A1 | 9/2005 | Torre et al. |
| 2005/0267595 A1 | 12/2005 | Chen et al. |
| 2005/0267596 A1 | 12/2005 | Chen et al. |
| 2006/0058829 A1 | 3/2006 | Sampson et al. |
| 2006/0184112 A1 | 8/2006 | Horn et al. |
| 2006/0259020 A1 | 11/2006 | Sharratt |
| 2007/0016262 A1 | 1/2007 | Gross et al. |
| 2007/0093728 A1 | 4/2007 | Douglas et al. |
| 2007/0100367 A1 | 5/2007 | Quijano |
| 2007/0100368 A1 | 5/2007 | Quijano |
| 2007/0100369 A1 | 5/2007 | Cragg |
| 2007/0142770 A1 | 6/2007 | Rioux et al. |
| 2007/0149994 A1 | 6/2007 | Sosnowski |
| 2007/0173881 A1 | 7/2007 | Birk et al. |
| 2007/0233161 A1 | 10/2007 | Weller et al. |
| 2007/0250020 A1 | 10/2007 | Kim et al. |
| 2007/0265369 A1* | 11/2007 | Muratoglu et al. ........... 522/157 |
| 2007/0265598 A1 | 11/2007 | Karasik |
| 2007/0288033 A1 | 12/2007 | Murature et al. |
| 2008/0058887 A1 | 3/2008 | Griffin et al. |
| 2008/0082056 A1 | 4/2008 | Mauch et al. |
| 2008/0097513 A1 | 4/2008 | Kaji et al. |
| 2008/0119729 A1 | 5/2008 | Copa et al. |
| 2008/0172079 A1 | 7/2008 | Birk |
| 2008/0190363 A1 | 8/2008 | Chen et al. |
| 2008/0208241 A1 | 8/2008 | Weiner et al. |
| 2008/0233167 A1 | 9/2008 | Li et al. |
| 2008/0243071 A1 | 10/2008 | Quijano |
| 2008/0243166 A1 | 10/2008 | Paganon et al. |
| 2008/0255601 A1 | 10/2008 | Birk |
| 2008/0319471 A1 | 12/2008 | Sosnowski et al. |
| 2009/0048624 A1 | 2/2009 | Alverdy |
| 2009/0275973 A1 | 11/2009 | Chen et al. |
| 2010/0023047 A1 | 1/2010 | Simpson |
| 2010/0130998 A1 | 5/2010 | Alverdy |
| 2010/0243135 A1 | 9/2010 | Pepper et al. |
| 2011/0178544 A1 | 7/2011 | Sosnowski et al. |
| 2012/0271336 A1 | 10/2012 | Hamman et al. |
| 2012/0289992 A1 | 11/2012 | Quijano et al. |

FOREIGN PATENT DOCUMENTS

| | | |
|---|---|---|
| EP | 0 485 903 | 8/1991 |
| FR | 2862525 A1 | 5/2005 |
| GB | 2 139 902 A | 11/1984 |
| WO | WO-0166166 A2 | 9/2001 |
| WO | WO 2006035446 | 4/2006 |
| WO | WO-2006056944 A1 | 6/2006 |
| WO | WO 2006/128978 | 12/2006 |
| WO | WO-2007027812 A2 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO-2008121831 A1 | 10/2008 |
| WO | WO-2009112786 A2 | 9/2009 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011038270 A2 | 3/2011 |
| WO | WO2011024077 | 8/2011 |
| WO | WO2011097637 | 8/2011 |
| WO | WO2011127205 | 10/2011 |
| WO | WO-2012048226 A1 | 4/2012 |

OTHER PUBLICATIONS

International Search Report; International Application No. PCT/US2011/031463; Applicant: ReShape Medical, Inc., Mailing Date: Jun. 27, 2011, 10 pages.

International Search Report and Written Opinion; International Applicaton No. PCT/US1155373, Applicant: Reshape Medical, Inc., Mailing Date Jan. 20, 2012, 7 pages.

Non-Final Office Action; U.S. Appl. No. 11/694,536; Mailing Date Oct. 26, 2011, 13 pages.

Non-Final Office Action; U.S. Appl. No. 12/625,473; Mailing Date Oct. 24, 2011, 18 pages.

(56) References Cited

OTHER PUBLICATIONS

International Search Report; International Application No. PCT/US2008/058677, Applicant: ReShape Medical et al., Mailing Date Aug. 21, 2008, 12 pages.

International Search Report; International Application No. PCT/US2006/042710, Applicant: Abdominus, Inc. et al., Mailing Date Mar. 15, 2007, 9 pages.

International Search Report; International Application No. PCT/US2006/048647, Applicant: Abdominus, Inc. et al., Mailing Date May 22, 2007, 12 pages.

International Search Report; International Application No. PCT/US2008/068058, Applicant: ReShape Medical, Inc. et al, Mailing Date Nov. 19, 2008, 11 pages.

International Search Report; International Application No. PCT/US2006/042711, Applicant: Abdominus, Inc. et al, Mailing Date Mar. 16, 2007, 9 pages.

Supplementary European Search Report for EP 03726447.0, mailed Mar. 1, 2006.

International Search Report; International Application No. PCT/US2003/012782, Applicant: Applied Medical Resources Corporation, Mailing Date Oct. 28, 2003, 7 pages.

International Search Report; International Application No. PCT/US2006/042336, Applicant: Abdominus, Inc., Mailing Date Mar. 14, 2007, 9 pages.

International Search Report; International Application No. PCT/US2010/029865, Applicant: ReShape Medical, Inc., Mailing Date Jan. 5, 2011, 9 pages.

International Search Report; International Application No. PCT/US2011/024082, Applicant: ReShape Medical, Inc., Mailing Date Apr. 6, 2011, 10 pages.

International Search Report; International Application No. PCT/US2011/024077; Applicant: ReShape Medical, Inc., Mailing Date Apr. 6, 2011, 12 pages.

International Search Report; International Application No. PCT/US2010/042948; Applicant: ReShape Medical, Inc., Mailing Date Apr. 1, 2011, 11 pages.

International Search Report; International Application No. PCT/US2010/043136; Applicant: ReShape Medical, Inc., Mailing Date Apr. 12, 2011, 9 pages.

Final Office Action; U.S. Appl. No. 11/694,536, Mailing Date Mar. 11, 2011, 13 pages.

Final Office Action; U.S. Appl. No. 11/768,152, Mailing Date Jan. 19, 2011, 13 pages.

International Search Report; International Application No. PCT/US2010/043134; Applicant ReShape Medical, Inc., Mailing Date Apr. 27, 2011, 12 pages.

International Search Report; International Application No. PCT/US2011/0426233; Applicant: ReShape Medical, Inc., Mailing Date Apr. 26, 2011, 9 pages.

"ReShape Inflatable Gastric Ballon Going on Trial as Weight Loss Option," MedGadget: Internet Journal of Emerging Medical Technologies. Feb. 4, 2010. (5 pages).

Wahlen CH et al. "The BioEnterics Intragastric Balloon: How to use it" Obesity Surgery 2001;11:524-527.

Patient information "Living with the BIB" by INAMED Health (2004).

Non-Final Office Action; U.S. Appl. No. 11/263,302; dated: Oct. 9, 2012, 6 pages.

Non-Final Office Action; U.S. Appl. No. 12/625,473; dated Jul. 12, 2012; 10 pages.

Non-Final Office Action; U.S. Appl. No. 12/723,545; dated Feb. 29, 2012, 10 pages.

Non-Final Office Action; U.S. Appl. No. 13/074,956; dated Oct. 1, 2012, 8pages.

European Supplementary Search Report; EP Application No. 10802994.3, Applicant: ReShape Medical, Inc., mailed Jun. 28, 2013, 8 pgs.

European Supplementary Search Report; EP Application No. 10802918.2, Applicant: ReShape Medical, Inc., mailed Jun. 5, 2013, 6 pgs.

\* cited by examiner

INTRAGASTRIC SPACE FILLERS AND METHODS OF MANUFACTURING INCLUDING IN VITRO TESTING

RELATED APPLICATIONS

This application claims the full Paris Convention benefit of and priority to U.S. Provisional Patent Application Ser. No. 61/166,675, filed on Apr. 3, 2009, the contents of which are incorporated by reference herein in its entirety, as if fully set forth herein.

BACKGROUND

This disclosure relates to implantable intragastric devices and systems and methods of in vitro testing of the same. More specifically, this disclosure relates to improvements to inflatable intragastric space filler devices to prevent undesired rupture and leakage.

SUMMARY

According to embodiments, disclosed is a process for manufacturing an intragastric device, comprising, in combination: providing a balloon having a body, a cuff extending from the body, and a collar at an end of the cuff; providing a shaft through the cuff and the collar of the balloon; folding the cuff on itself within the body of the balloon, whereby the cuff is brought to the body of the balloon and whereby the cuff forms overlapping surfaces and a folded inner surface; adhering the overlapping surfaces of the cuff to each other at a balloon-to-balloon interface; adhering the folded inner surface to the shaft at a balloon-to-shaft interface. A product may be produced thereby.

The overlapping surfaces of the cuff may be adhered to each other with a silicone-based adhesive. The adhesive may have a hardness about the same as the hardness of the balloon. The folded inner surface may be adhered to the shaft with a silicone-based adhesive. The adhesive may have a hardness less than the hardness of the shaft.

According to embodiments, disclosed is an improved process for manufacturing intragastric space fillers, which comprises, in combination: providing the intragastric device having a balloon and a shaft extending through the balloon, the shaft fixed to the balloon, wherein the balloon and the shaft form a balloon-to-shaft transition where an exposed surface portion of the balloon meets with an exposed surface portion of the shaft; providing a surface fillet across at least the balloon-to-shaft transition. A product may be produced thereby.

The surface fillet may be a sheet bonded by an adhesive. The sheet may form a washer concentric with the shaft. The surface fillet may be an adhesive. The surface fillet may be silicone-based. The surface fillet may have a hardness between a hardness of the shaft and a hardness of the balloon. The surface fillet may reduce stress concentrations near the transition section to facilitate a smoother transition from balloon to shaft. The process may further comprise: providing a second surface fillet across at least a second balloon-to-shaft transition.

According to embodiments, disclosed is a kit, comprising, in combination: a shaft; a balloon having a body and two cuffs, each with a collar at an end thereof, the cuffs configured to receive the shaft through the two cuffs and the body of the balloon while in an assembled state, wherein the shaft and balloon form at least one balloon-to-shaft transition where an exposed surface portion of the balloon meets with an exposed surface portion of the shaft while in the assembled state; a surface fillet configured to be placed across the balloon-to-shaft transition while in the assembled state, wherein the surface fillet reduces stress concentrations near the balloon-to-shaft transition to facilitate a smoother transition from balloon to shaft. The shaft and the surface fillet may be in the assembled state.

According to embodiments, disclosed is an intragastric device, comprising, in combination: a shaft having shore durometer hardness of at most about 55A; a balloon having shore durometer hardness of at least about 20A and comprising a body, a cuff extending from the body, and a collar at an end of the cuff; a surface fillet across the exposed surface portion of the balloon and the exposed surface portion of the shaft at a balloon-to-shaft transition, the surface fillet having a hardness between the hardness of the shaft and the hardness of the balloon.

The surface fillet may be a sheet bonded by an adhesive. The sheet may form a washer concentric with the shaft. The surface fillet may be an adhesive.

According to embodiments, disclosed is an intragastric device, comprising, in combination: a shaft; a balloon comprising a body, a cuff extending from the body, and a collar at an end of the cuff; wherein an interior portion of the body has an inner fillet having a thickness greater than a thickness of an equator of the balloon and configured to transition an interior wall of the balloon to at least one of the shaft and the cuff when folded within the body of the balloon.

According to embodiments, disclosed is an in vitro testing process for accelerated simulation of conditions in a stomach, in combination: providing an intragastric device to an acetone bath; inducing swelling of the intragastric device; exacerbating weak spots in the intragastric device.

The process may further comprise observing the results and estimating the results of an in vivo study. The swelling may be induced in proportion to the permeability of the intragastric device. The acetone bath may contain at least about 95% acetone by volume. The acetone bath may be provided at room temperature. The intragastric device and the acetone bath may be maintained in a sealed environment. A time to failure of the intragastric device in the in vitro testing process may be linearly related to a projected time to failure in an in vivo study.

According to embodiments, disclosed is an in vitro testing process for accelerated simulation of conditions in a stomach, comprising, in combination: providing an intragastric device to a hydrochloric bath of pH between about 1.0 and about 1.5, heated to between about 50° C. and about 60° C.; exacerbating weak spots in the intragastric device.

The process may further comprise: observing the results and estimating the results of an in vivo study.

According to embodiments, disclosed is a process for manufacturing a balloon of an intragastric device, comprising, in combination: subjecting materials for the balloon to a heated environment, whereby between about 85% and about 95% of a target property for the balloon is achieved by partial cross-linking; removing the balloon from the heated environment, whereby additional cross-linking is achieved and driven by residual heat retained from the heated environment; and subjecting the balloon to radiation-based sterilization, whereby about 100% of the target property is achieved. A product may be produced thereby.

The target property may be resistance to failure when subjected to a mechanical stress. The target property may be resistance to failure when subjected to a mechanical stress. The mechanical stress may be torque. The mechanical stress may be elongation. The target property may be tensile strength. The target property may be resistance to ingress and egress across walls of the balloon. The materials for the balloon may be silicone-based. The radiation-based sterilization may be gamma sterilization.

DRAWINGS

Figure 2:
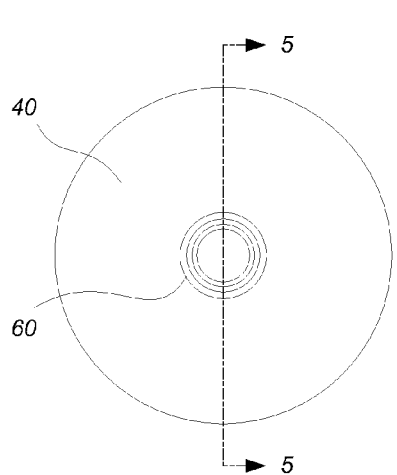
Figure 3:
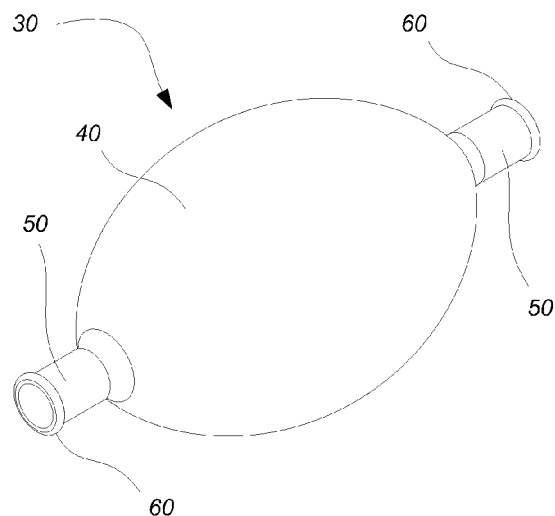
Figure 4:
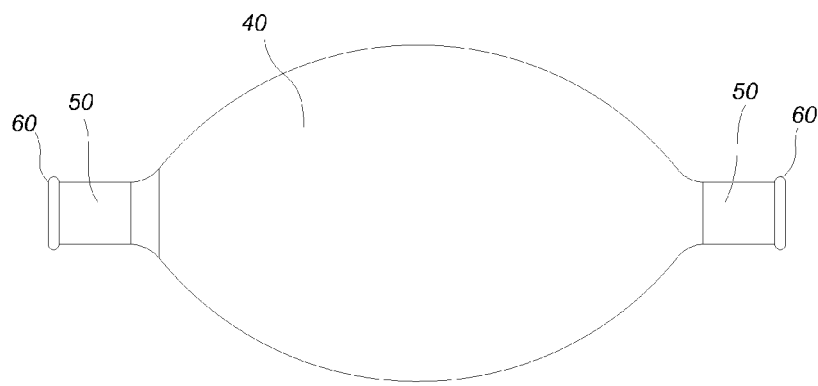
Figure 5:
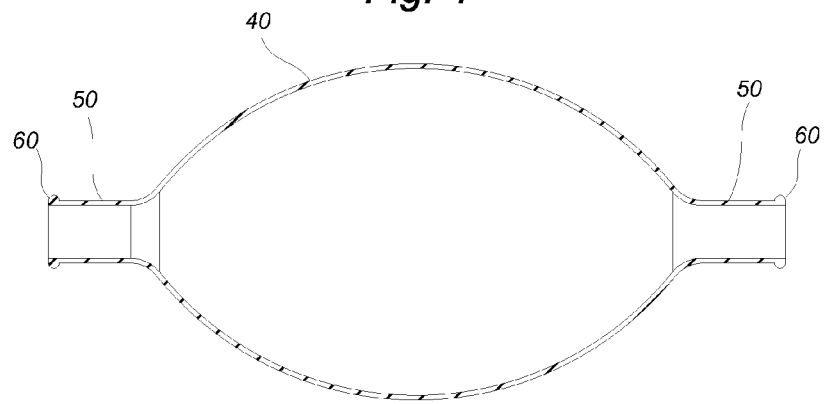
Figure 6:
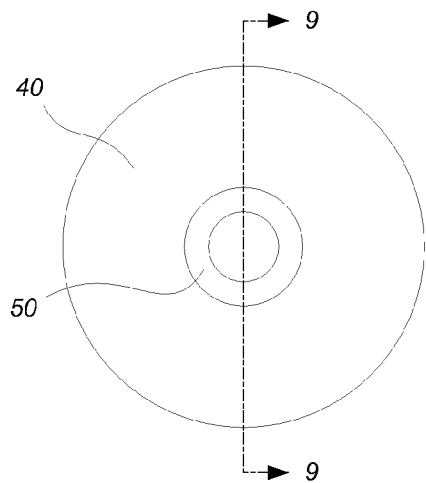
Figure 7:
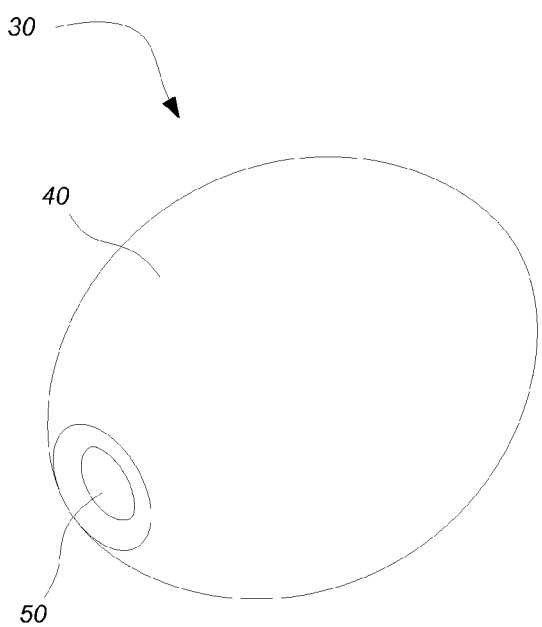
Figure 8:
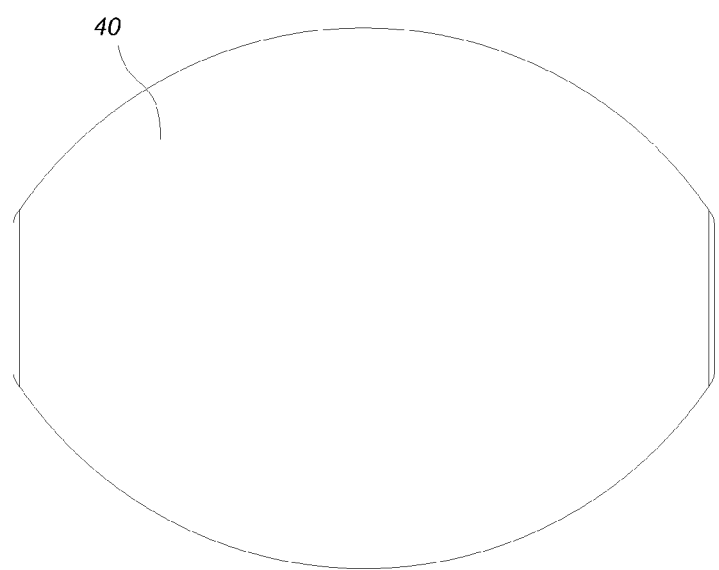
Figure 9:
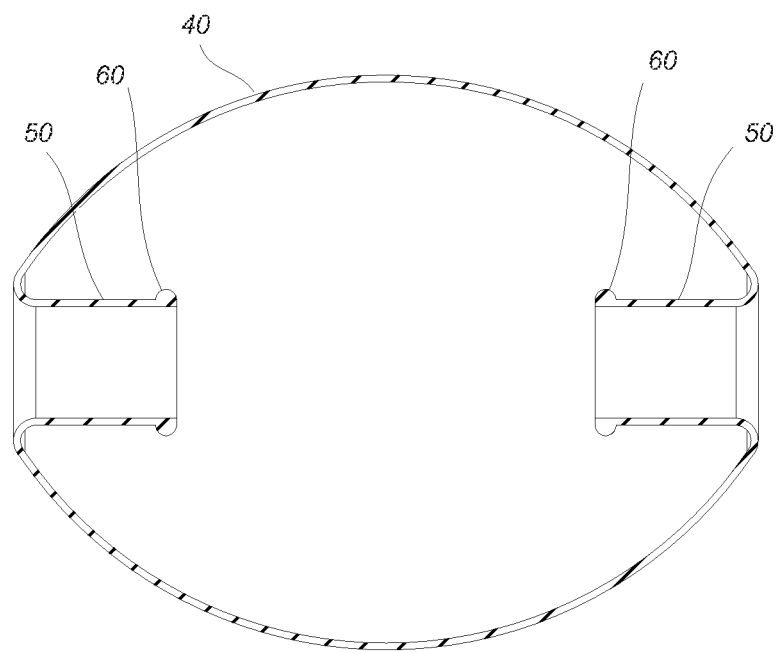
Figure 10:
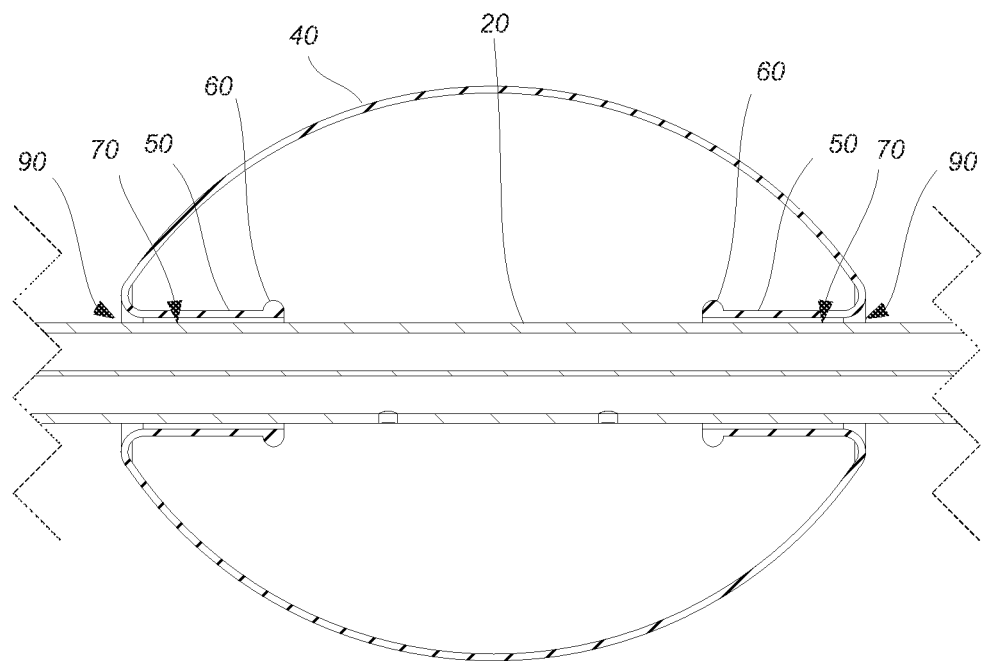
Figure 11:
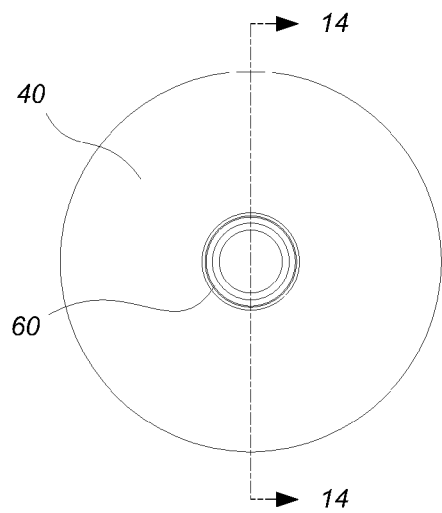
Figure 12:
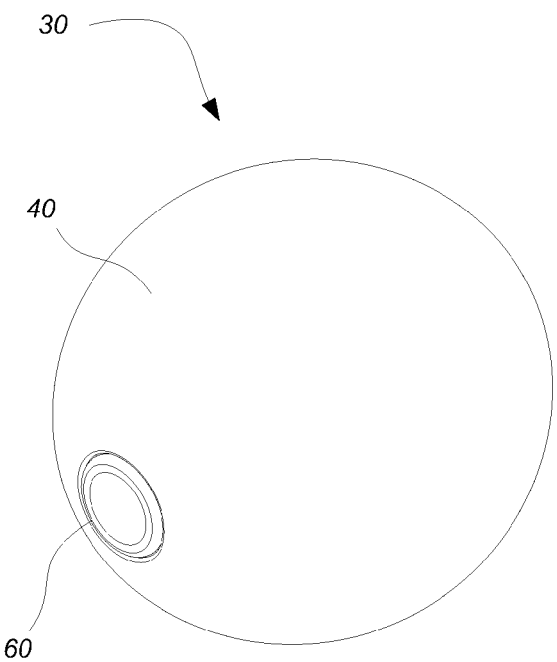
Figure 13:
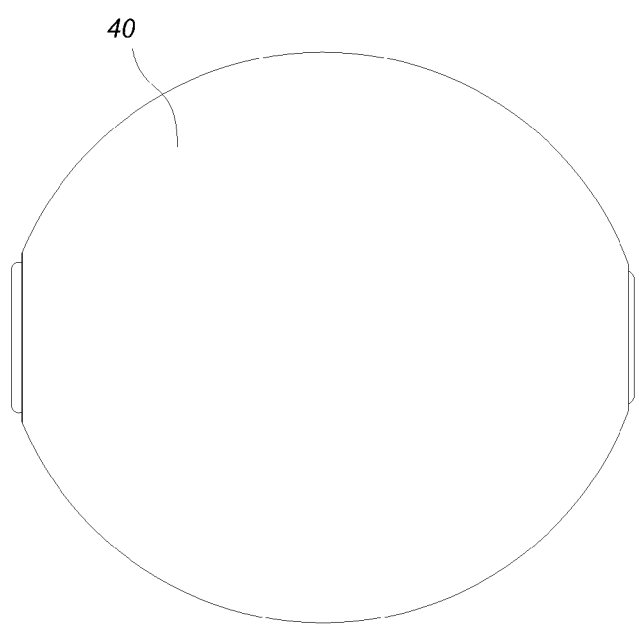
Figure 14:
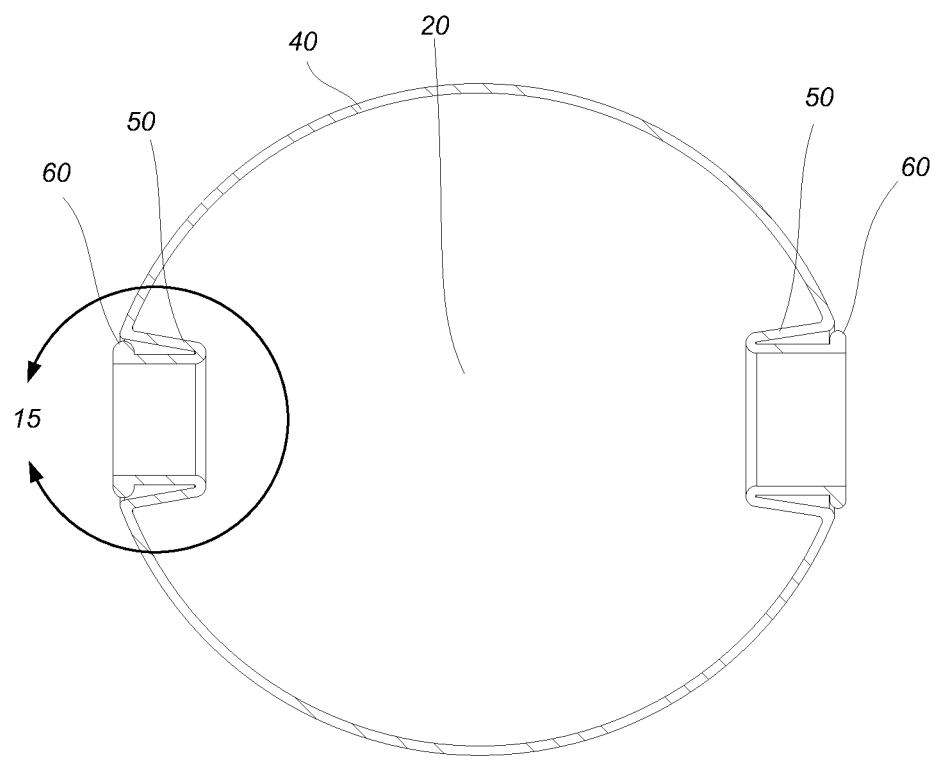
Figure 15:
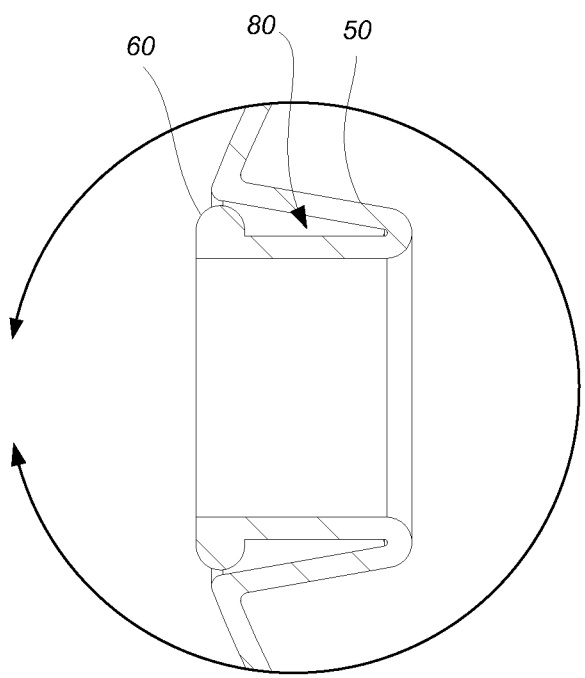
Figure 16:
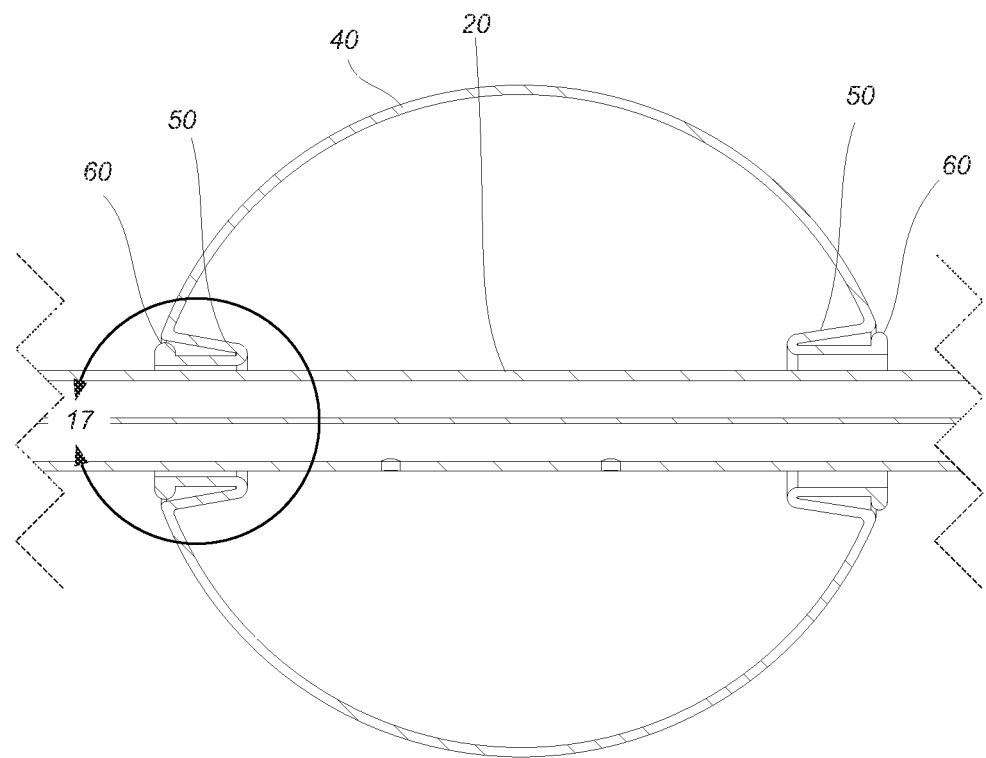
Figure 17:
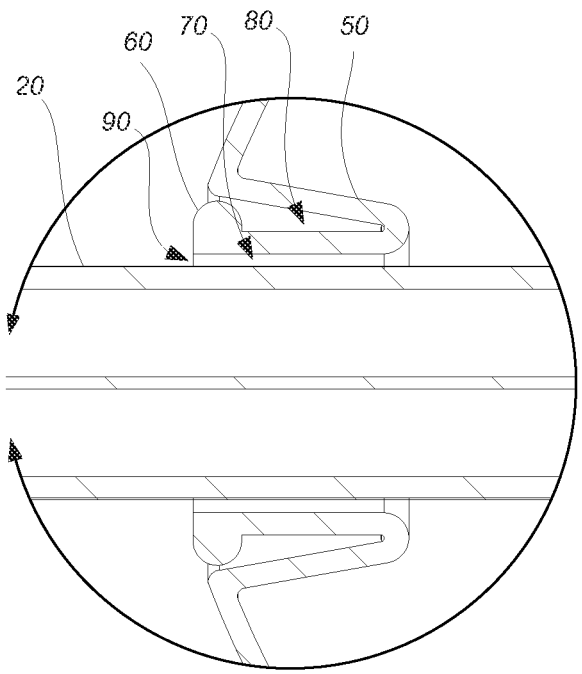
Figure 18:
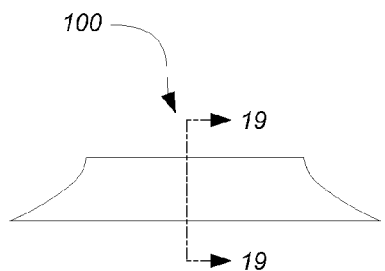
Figure 19:
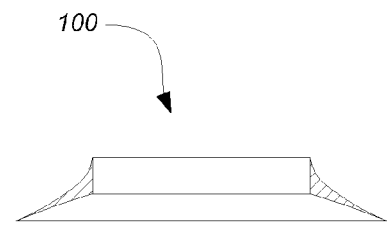
Figure 20:
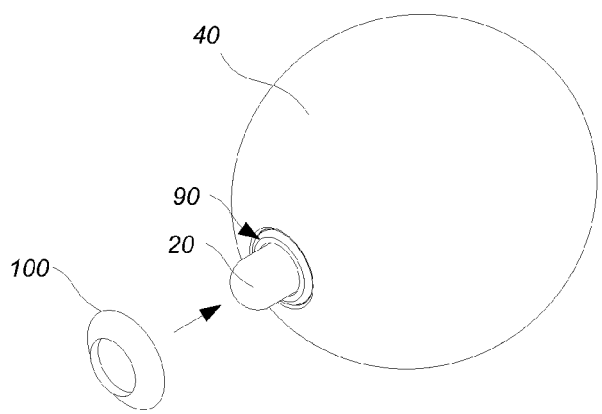
Figure 21:
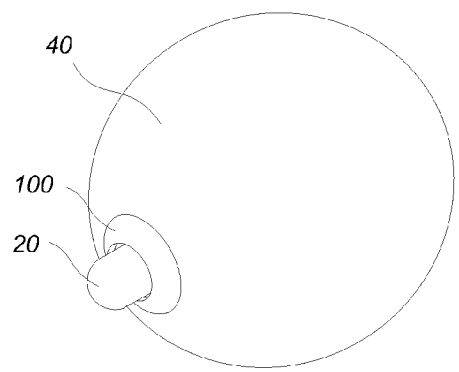
Figure 22:
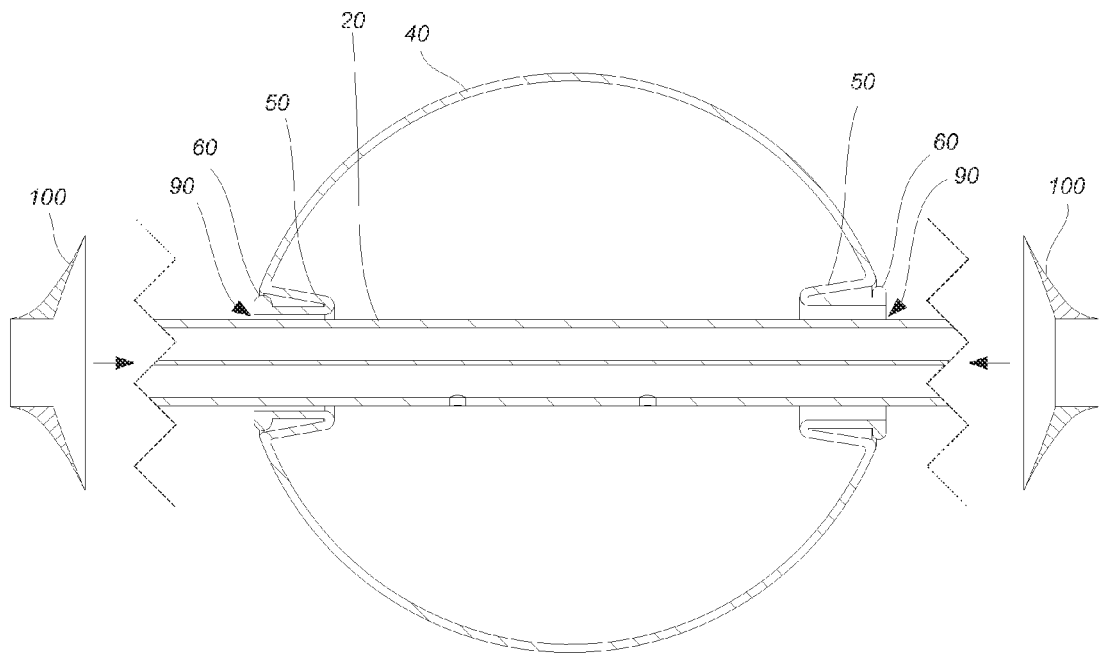
Figure 23:
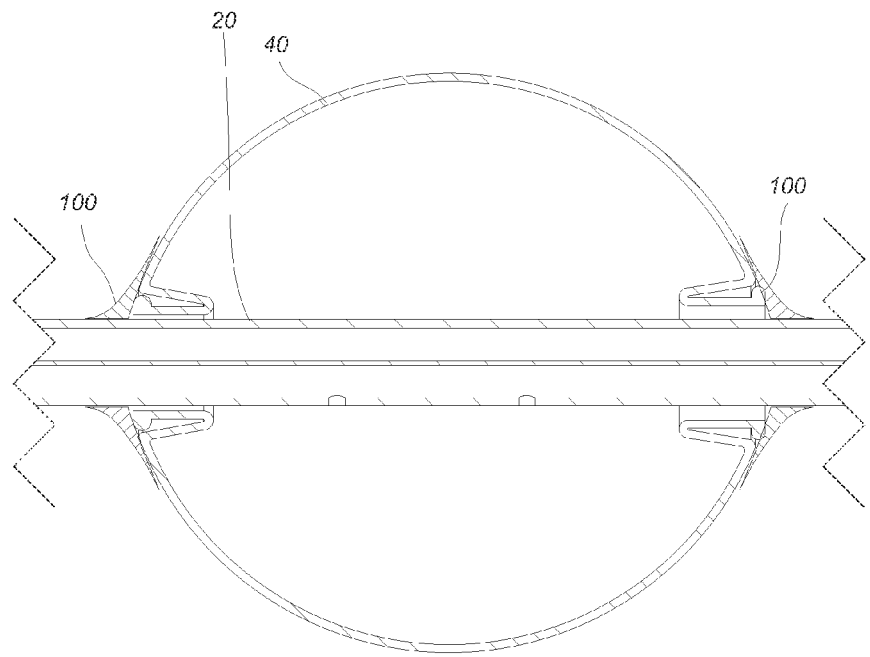
Figure 24:
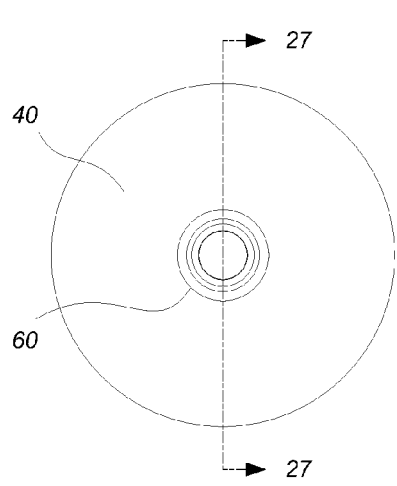
Figure 25:
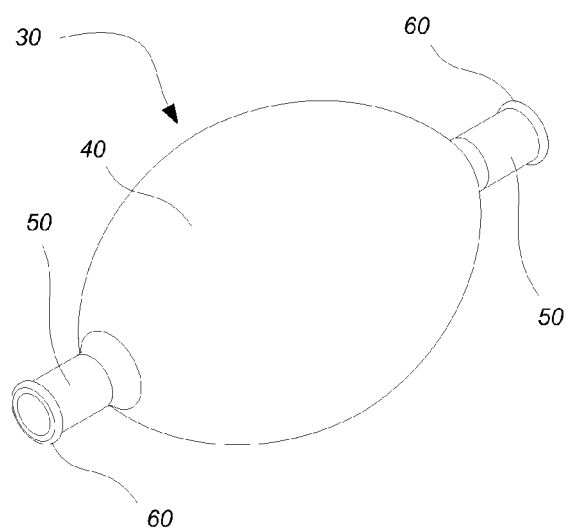
Figure 26:
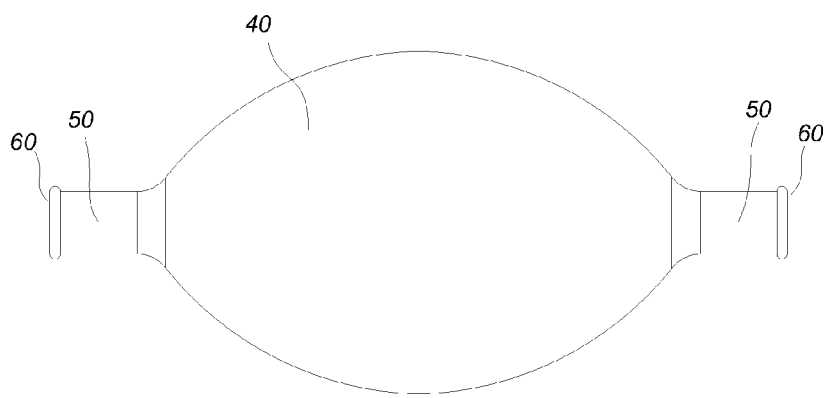
Figure 27:
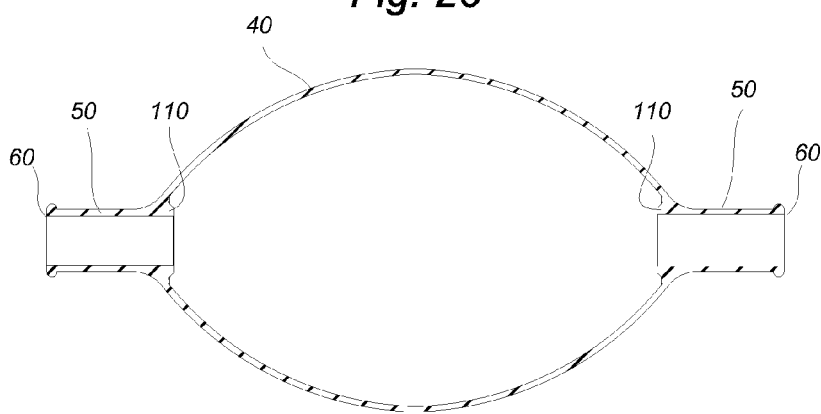
Figure 28:
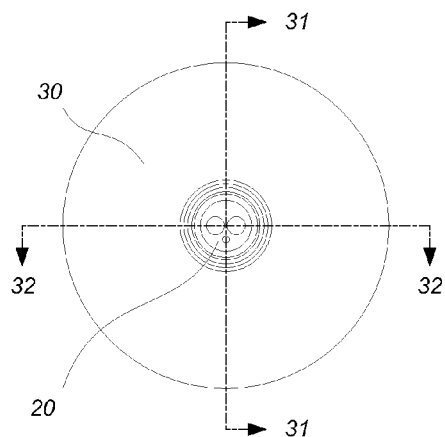
Figure 29:
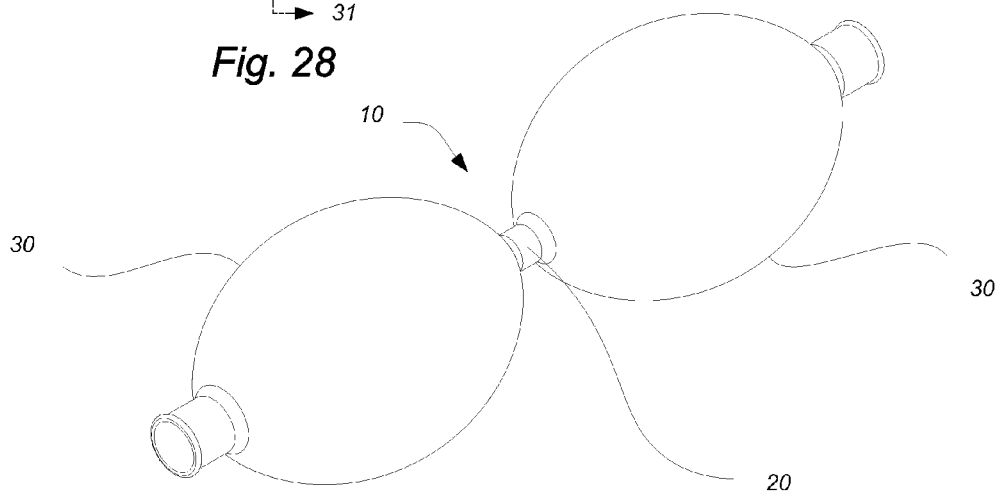
Figure 30:
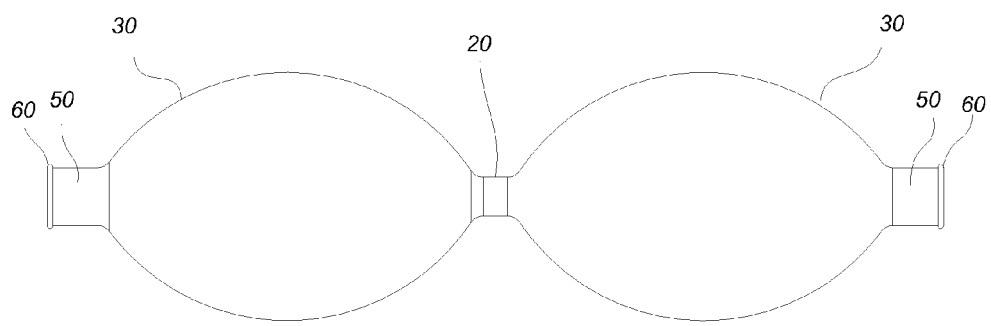
Figure 31:
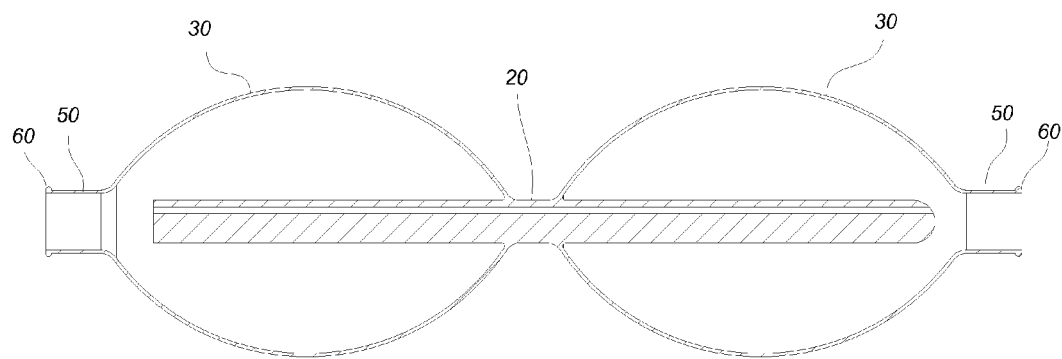
Figure 32:
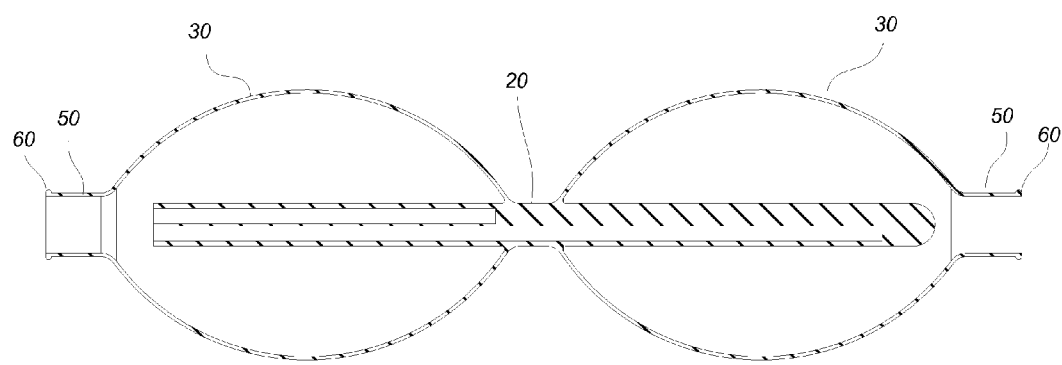
Figure 33:
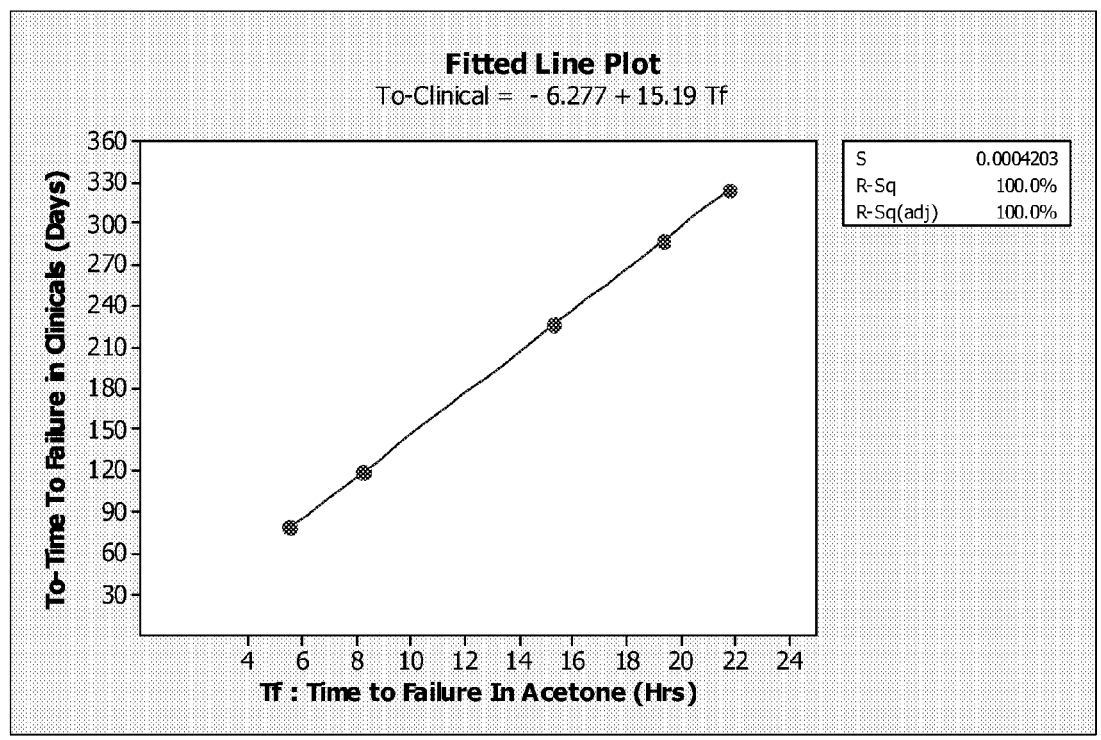
Figure 34:
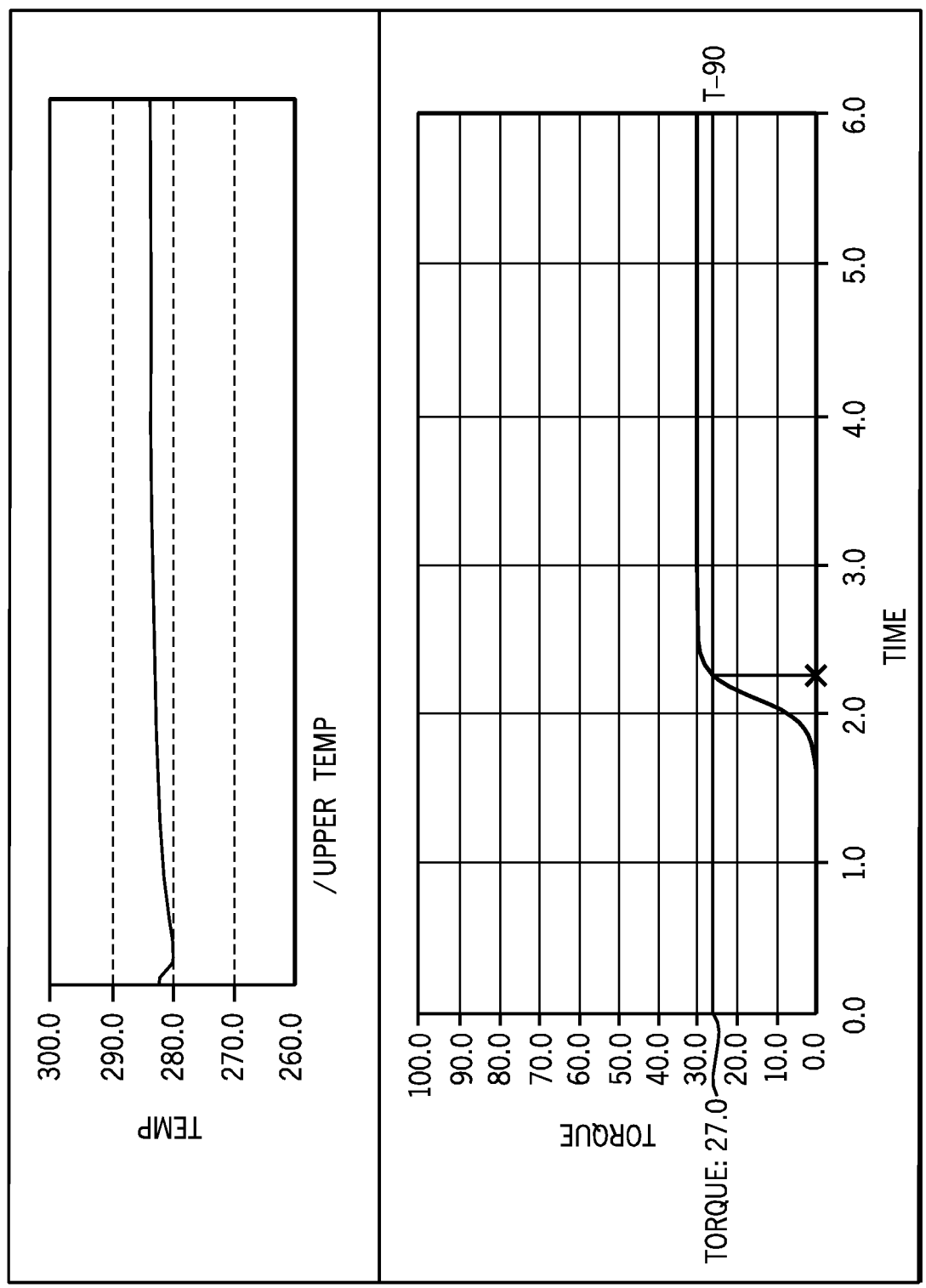

The above-mentioned features and objects of the present disclosure will become more apparent with reference to the following description taken in conjunction with the accompanying drawings wherein like reference numerals denote like elements and in which:

FIG. 1 shows a perspective view of an intragastric space filler;
FIG. 2 shows a front view of a balloon;
FIG. 3 shows a perspective view of a balloon;
FIG. 4 shows a side view of a balloon;
FIG. 5 shows a sectional view of a balloon;
FIG. 6 shows a front view of a balloon;
FIG. 7 shows a perspective view of a balloon;
FIG. 8 shows a side view of a balloon;
FIG. 9 shows a sectional view of a balloon;
FIG. 10 shows a sectional view of a balloon and shaft;
FIG. 11 shows a front view of a balloon;
FIG. 12 shows a perspective view of a balloon;
FIG. 13 shows a side view of a balloon;
FIG. 14 shows a sectional view of a balloon;
FIG. 15 shows a sectional view of a balloon;
FIG. 16 shows a sectional view of a balloon and shaft;
FIG. 17 shows a sectional view of a balloon and shaft;
FIG. 18 shows a side view of an outer fillet;
FIG. 19 shows a sectional view of an outer fillet;
FIG. 20 shows a perspective view of an outer fillet approaching an intragastric space filler;
FIG. 21 shows a perspective view of an outer fillet on an intragastric space filler;
FIG. 22 shows a sectional view of an outer fillet approaching an intragastric space filler;
FIG. 23 shows a sectional view of an outer fillet on an intragastric space filler;
FIG. 24 shows a front view of a balloon;
FIG. 25 shows a perspective view of a balloon;
FIG. 26 shows a side view of a balloon;
FIG. 27 shows a sectional view of a balloon;
FIG. 28 shows a front view of a one-piece intragastric space filler;
FIG. 29 shows a perspective view of a one-piece intragastric space filler;
FIG. 30 shows a side view of a one-piece intragastric space filler;
FIG. 31 shows a sectional view of a one-piece intragastric space filler;
FIG. 32 shows a sectional view of a one-piece intragastric space filler;
FIG. 33 shows a graph having data plots and a fitted line plot of results of an embodiment of the present disclosure comparing a time to failure of an intragastric space filler in an in vitro acetone bath (x-axis in hours) and a time to failure of an embodiment of an intragastric space filler for in vivo clinical trials (y-axis in days); and
FIG. 34 shows a sample chart with curing parameters.

DETAILED DESCRIPTION

The inventors of the present disclosure have observed late stage deflations with inflated intragastric balloon devices used in clinical trials. The deflations indicate certain wear-out mechanisms—in particular, in the area between balloon-to-shaft (BTS) bonds. During in vivo tests, these manifest as balloon deflations after months within the stomach.

According to embodiments, and as shown in FIG. 1, intragastric device 10 is a medical device configured to be emplaced within a gastric cavity of a patient for a duration of time. Intragastric device 10 may include shaft 20 with at least one balloon 30 disposed thereon. Shaft 20 may extend through one or more balloons 30. Shaft 20 may provide structure, interfacing for implant or explant, or components for inflation or deflation of one or more balloons 30.

According to embodiments, balloon 30 is any expandable, space filling component. Balloon 30 may have any variety of geometries and shapes. As shown in FIGS. 2, 3, 4, and 5, balloon 30 may include body 40, with at least one cuff 50 extending from body 40 for interfacing with other components, such as shaft 20 extending through balloon 30. Collar 60 may be provided at an end of cuff 50. Collar 60 may be thinner or thicker than cuff 50 or be tapered, scalloped, rounded, cornered, etc. Balloon 30 may be an open or closed balloon. Balloon 30 and parts thereof may have an inner surface and outer surface.

According to embodiments, cuff 50 of balloon 30 may be folded to within body 40 of balloon 30, as shown in FIGS. 6, 7, 8, 9, and 10. In such a position, at least a portion of cuff 50 may be configured to interface with shaft 20. As shown in FIG. 10, balloon-to-shaft (BTS) interface 70 is defined as the areas at which balloon 30 and shaft 20 are bonded together. For example, BTS interface 70 may be where cuff 50 is bonded to shaft 20. According to embodiments, BTS interface 70 may be disposed within body 40 of balloon 30. At BTS interface 70, at least one adhesive may be provided or at least one of balloon 30 and shaft 20 may be modified so as to form a fixation of balloon 30 relative to shaft 20.

According to embodiments, as shaft 20 extends through balloon 30, balloon-to-shaft (BTS) transition 90 is defined as one or more meeting places relative to an external (exposed) portion of balloon 30 and an external (exposed) portion of shaft 20. For example, BTS transition 90 may be the point at which balloon 30 and shaft 20 meet to begin BTS interface 70.

According to embodiments, intragastric device 10 with at least one balloon 30 may be configured for use as an implantable device within a gastric cavity. Where implant is temporary, intragastric device 10 must be explanted after some period of time. Durability and longevity of intragastric device 10 may be defined, at least in part, by characteristics of balloon 30. Balloon 30 may be subjected to harsh gastric environments for an extended amount of time. Accordingly, the materials and manufacturing methods of the materials are key contributors as to balloon integrity and longevity.

According to embodiments, intragastric device 10 may experience rupture, tearing, wear-out, degradation, or leakage of a balloon at or near BTS interface 70 or BTS transition 90. According to embodiments, various improvements to embodiments of intragastric space fillers are disclosed herein. Such improvements apply to devices as disclosed herein, to devices as incorporated by reference, and to devices known in the art, as artisans will appreciate.

According to embodiments, accelerated in vitro models for silicone creep/stress relaxation failure are disclosed. According to embodiments, said in vitro models closely approximate the results observed during in vivo testing. Thereby, said models provide a standard by which intragastric devices may be tested for durability and performance, where the results project a hypothetical in vivo experience similar to the in vitro results.

In order to identify mitigations in a rapid manner for the observed wear-out mechanism, an accelerated in vitro wear-out model was developed and several engineering solutions identified. Multiple environmental tests were developed in an attempt to accelerate the in vitro testing while re-creating the observed in vivo wear-out mechanisms. One test involved a low pH (1.0-1.5) heated bath and the other used an acetone bath at ambient temperature. As part of testing, multiple configurations of a balloon subassembly with process enhancements were subjected to the environmental tests. According to embodiments, the Acetone bath reproduced seemingly identical deflation modes to those observed in the in vivo clinical trials.

According to embodiments, a heated low ph (1.0-1.5) hydrochloric bath creates an accelerated (through increased heat and ambient temperature adjusted to 37° C.) in vitro stomach environment (low pH). The test method may exacerbate any weak spots in the balloon assembly in an accelerated fashion.

According to embodiments, hydrochloric bath tests did produce failures in intragastric space fillers, but they were not uniformly produced in the BTS area as seen in the clinical units. The time to failure ranged from 15-112 hours after the start of testing. All failures were located in the equator region of the balloon. The heated low pH bath test serves as an acute failure test of overall balloon integrity at a moderate temperature (50-60° C.).

According to embodiments, an acetone bath creates an accelerated in vitro stomach environment. Acetone, as a solvent, induced swelling (up to 180% of the original size, from Dow Corning Form #45-0113D-01, Silicone Rubber: Fluid Resistance Guide (2005). The induced stress exacerbates any weak spots in a balloon in an accelerated fashion in an effort to recreate the deflations found during in vivo clinical trials.

According to embodiments, the volume of solvent used for each test sample remains constant for solvent concentration consistency. The bath may contain between about 95% to about 100% acetone by volume. The test may be performed at room temperature, with a test sample and bath contents in a sealed, air-tight container.

According to embodiments, balloon samples soaked in acetone tend to become stiffer, whereby they achieve reduced elongation and tensile abilities due to a higher modulus. The stress relaxation becomes slower, yielding lower creep rates. Additionally, the balloon is swelling (osmosis of acetone into the balloon cavity & vice versa for saline & methylene blue expelling through the open pores, confirmed by blue tint in acetone bath during prolonged testing) and building up volume, inducing more stress as test time increases. The stress is dependent on the size of the balloon (larger balloon means larger stresses) and its porosity and permeability.

Baseline and multiple product enhancements and configurations were subjected to the acetone bath test. 40 of 42 failed at the bonding area between the shaft and balloon, one unit failed at the equator, and other enhanced units did not fail. This test method did successfully recreate the failures in a repeatable manner (all standard clinical configuration and enhancement units failed in the bonded region between the shaft and balloon).

FIG. 33 shows a graph having data plots and a fitted line plot of results of an embodiment of the present disclosure comparing a time to failure of an embodiment of an intragastric space filler in acetone (x-axis in hours) with a time to failure of an embodiment of an intragastric space filler in clinical trials (y-axis in days). The correlation between in vitro acetone wear-out models and in vivo models for intragastric balloons is shown. Data points are provided, as well as a fitted plot line, demonstrating the essentially linear relationship between in vitro and in vivo models (R and $R^2$ values of 100.0%).

According to embodiments, balloon-to-shaft (BTS) regions are subjected to considerable radial expansion when removing balloon 30 from a mandrel after a molding process. Because the widest portion of the mandrel must pass through cuff 50, expansion thereof may be high (exceeding 500% in some cases). This may leave balloon 30 with permanent stress marks, which may manifest as device failure in late stage operation. Studies were conducted comparing BTS regions near each of (1) cuffs through which mandrels were removed and (2) cuffs unexpanded during the molding process. BTS regions subjected to expansion during mandrel removal showed statistically lower tensile abilities by in vivo and in vitro testing.

According to embodiments, an improved configuration for intragastric device 10 is disclosed. According to embodiments, as shown in FIGS. 11, 12, 13, 14, and 15, cuff 50 may be folded upon itself within body 40 of balloon 30, whereby cuff 50 forms overlapping surfaces. As shown in FIGS. 14 and 15, cuff 50 may form bi-layered cuff 50, whereby balloon-to-balloon (BTB) interface 80 is created. Cuff 50 may be bonded to itself at BTB interface 80, for example, with adhesive. The bonding may occur by applying adhesive to an outer portion of the cuff 50, which becomes folded onto itself to form BTB interface 80.

According to embodiments, folding cuff 50 causes collar 60 to be brought to body 40. For example, as shown in FIGS. 11, 12, 13, 14, and 15, collar 60 may be flush with, in contact with, or otherwise brought into close proximity to body 40. Collar 60 may have a geometry that provides a natural fillet between body 40 and shaft 20.

According to embodiments, as shown in FIGS. 16 and 17, shaft 20 may extend through balloon 30 including folded bi-layered cuff 50. According to embodiments, bi-layered cuff 50 includes a folded inner surface defined as the portion of cuff 50 facing shaft 20. In such a configuration, BTS interface 70 is defined as between the folded inner surface of cuff 50 and the portion of shaft 20 contacted thereby. According to embodiments, balloon 30 may be bonded to shaft 20 at BTS interface 70.

According to embodiments, at least one of cuff 50 and collar 60, rather than body 40, may form BTS transition 90 to shaft 20, as shown in FIGS. 16 and 17. Where body 40 is prevented from being directly bonded to shaft 20, bi-layered cuff 50 and adhesive layers may distribute stress concentrations from shaft 20 to body 40. Thicker layers of flexible materials may thereby be provided between body 40 and shaft 20.

According to embodiments, balloons 30 with bi-layered cuffs 50 showed improved performance relative to balloons 30 with single-layered cuffs 50 during an in vitro study in an accelerated in vitro test environment utilizing an acetone bath (average time to failure improved from 7.57 hours with single-layer to 74.57 hours with bi-layer).

According to embodiments, one or more BTS transitions 90 at one or more ends of balloon 30 may be provided with enhanced stress distribution by an improved mechanical joint reinforcement. For example, surface fillet 100 may be provided, as shown in FIGS. 18 and 19. Surface fillet 100 may be any structure configured to be placed at BTS transition 90 across at least an exposed surface of balloon 30 and an exposed surface of shaft 20. Surface fillet 100 may be a sheet in the form of a washer and be configured to be placed concentric with shaft 20. Surface fillet 100 may be integrated into balloon 30 or shaft 20 at a component level.

According to embodiments, surface fillet 100 may be flexible. For example, surface fillet 100 may be silicone-based. According to embodiments, surface fillet 100 has a hardness (durometer) less than that of shaft 20. For example, surface fillet 100 may have a hardness between the hardness of shaft 20 and the hardness of the balloon 30, to more evenly distribute and reduce stress concentrations transferred there between.

According to embodiments, a process is disclosed, comprising adding (e.g., bonded with adhesive) surface fillet 100 to BTS transition 90. For example, FIGS. 20 and 22 show surface fillet 100 approaching intragastric device 100. FIGS. 21 and 23 show surface fillet 100 bonded to intragastric device 100.

According to embodiments, intragastric space fillers with washers as surface fillets 100 showed improvement over those without washers during an in vitro study in an accelerated in vitro test environment utilizing an acetone bath (average time to failure improved from 7.57 hours without washers to 21.18 hours with washer).

According to embodiments, surface fillet 100 is an adhesive. For example, surface fillet 100 may be provided to BTS transition 90 in liquid form. Subsequently, surface fillet 100 may cure, dry, or otherwise resolve to a final form. Surface fillet 100 in its final form may have a hardness (durometer) less than that of shaft 20. The adhesive may be silicone-based.

According to embodiments, surface fillet 100 as an adhesive is provided in a process. The process involves adding more adhesive (e.g., silicone material) in the region of BTS transition 90 to help transition balloon 30 to shaft 20 as a bond (mechanical joint) in a smoother fashion (reduce stress concentration). Surface fillet 100 may be the same as or different from an adhesive provided at BTB interface 80.

Providing an adhesive surface fillet 100 showed improvement over standard balloon units during an in vitro study in an accelerated in vitro test environment utilizing an acetone bath (average time to failure improved from 7.57 hours without adhesive surface fillet to 13.25 hours with adhesive surface fillet).

According to embodiments, balloon 30 may include inner fillet 110, as shown in FIGS. 24, 25, 26, and 27. Inner fillet 110 may be molded in during formation of balloon 30 and may be provided to relieve stress on the balloon as a molded-in stress relievers. A portion of inner fillet 110 may be placed and configured to contribute to BTS interface 70. A portion of inner fillet 110 may be placed and configured to contribute to BTB interface 80.

According to embodiments, wall thickness of balloon 30 increases from the equator (midpoint between cuffs 50) thereof to the region of BTS transition 90. For example, the thickness may increase from about 0.030" at the equator to about 0.032" at or near BTS transition 90.

According to embodiments, shaft 20 of intragastric device 10 and balloon 30 of intragastric device 10 have disparate hardness. Balloons 30 may be of low durometer, such as shore 20A. Balloons 30 may be of silicone and formed by a molding process. Shaft 20 may be of higher durometer, such as shore 80A. Shaft 20 may be of silicone and formed by an extrusion process. Surface fillet 100 may be of silicone with durometer shore 24A. The steep transition of low to high durometer materials from 20A to 24A to 80A may provide for an uneven stress distribution while under load.

According to embodiments, the durometer of shaft 20 may be reduced from 80A to 55A (31% reduction). Thereby, stress is more evenly distributed between shaft 20 and balloon 30. This enhancement showed improvement over standard balloon units during an in vitro study in an accelerated in vitro test environment utilizing an acetone bath (average time to failure improved from 7.57 hours with 80A shaft to 41.07 hours with 55A shaft).

According to embodiments, intragastric device 10 may be a single molded piece that includes shaft 20 and at least one balloon 30, as shown in FIGS. 28, 29, 30, 31, and 32. Each balloon 30 may be integrally connected to shaft 20 with at least one connection point, as shown in FIGS. 31 and 32. For example, each balloon 30 may be integrally connected to shaft 20 at one end and have another end (i.e., with cuff 50 and collar 60) open for removal of a mandrel after a molding step.

A one-piece balloon assembly may be produced by a single molding step, rather than separate steps for respective components followed by combination thereof. Thus, a one-piece balloon assembly may have reduced assembly time. Where balloons 30 remain open, cuff 50 and collar 60 may be adhered to collar 20, for example by methods and processes disclosed herein.

A one-piece balloon assembly may have reduced stress concentrations by virtue of reduced bond joints requiring adhesive or other attachments provided. A one-piece balloon assembly may also provide reduction in assembly time by reducing the number of cuffs 50 that must be adhered to shaft 20.

According to embodiments, one or more kits may be provided containing one or more component. The components may include any of the devices or components thereof according to embodiments as disclosed herein. For example, one or more of shaft 20, balloon 30, and surface fillet 100 may be provided in a kit. The components of the kit may be assembled configured or adapted for assembly according to embodiments as disclosed herein. Accordingly, the components may be provided in an assembled state or in an unassembled state.

According to embodiments, enhanced processes for generating balloons and other components of intragastric device 10 are disclosed. According to embodiments, components of intragastric device 10, such as balloons 30, may have at least one target property. As used herein, a target property is a feature of a component of intragastric device 10 that is desirable or required. A target property may be one that provides satisfactory resistance or resilience to undesirable results, such as rupture, tear, creep, ingress, egress, or failure of intragastric device 10. Such results may be characterized by any effect that would be undesirable or unsafe during emplacement in, treatment of, or removal from a patient. A target property may be one or more of tensile strength, elasticity, porosity, etc. A target property may be one that provides satisfactory resistance or resilience to torque, elongation, compression, harsh chemical environment, etc.

During a curing cycle, materials used to form components of intragastric device 10 may be provided for molding. The materials may include any biocompatible polymer, such as silicone and silicone-based materials. During a curing cycle, the polymer may undergo cross-linking. A curing cycle may include exposure of the materials to heat while in a mold. According to embodiments, the extent of exposure to heat over time determines the extent of cross-linking, which thereby determines whether or to what degree the material approaches or reaches a target property.

According to embodiments, the materials may be exposed to a heated environment based on curing parameters until they have achieved less than about 100% of the target property. As used herein, curing parameters are conditions under which curing cycle is performed (e.g., temperature, time, etc.). For example, a curing cycle may continue until the materials achieve between about 80% and about 99% of the target property. More specifically, a curing cycle may continue until the materials achieve about 90% of the target property.

According to embodiments, the materials may be removed from the heated environment prior to achieving about 100% of the target property. The materials may retain at least some residual heat, whereby they may further approach, achieve, or exceed the target property.

According to embodiments, the materials may undergo a sterilization operation. During sterilization, the material may further approach, achieve, or exceed the target property. Sterilization may provide heat or otherwise result in additional cross-linking of the material. Sterilization may include exposure to radiation (e.g., gamma rays, electron beams, X-rays, ultraviolet light, subatomic particles, etc.). For example, where a curing cycle and residual heat are insufficient to achieve about 100% of the target property, the sterilization may be sufficient to do so.

According to embodiments, curing parameters may be determined based on the target property and the material (i.e., material lot). For example, where a silicone material was used and gamma sterilization was performed, the material was determined to achieve between about 90% and about 100% of its exemplary target property (i.e., torque) after being cured to 90% of the same target property by the heated environment (i.e., at 285° C.±5° C.) and residual heat thereafter. As shown in FIG. 34, a material may have a known progression toward a target property over time at a given temperature. Such information may often be obtained by a materials provider. According to embodiments, as shown in FIG. 34, a certain material may asymptotically approach 30.0 points on the torque curve. The point in time at which it reaches 90% (27.0 points on the torque curve) may be determined, thereby yielding a curing parameter of the curing cycle. The curing parameters may accommodate the effect of residual heat after removal from the heated environment as well as the effect of sterilization. For example, the remaining 10% of the curing (cross-linking) occurred while the materials were waiting to be removed off the mold and during gamma sterilization.

According to embodiments, this enhancement showed improvement over standard balloon units during an in vitro study in an accelerated in vitro test environment utilizing an acetone bath (average time to failure improved from 7.57 hours in standard units to 41.54 hours based on an embodiment of the above method).

According to embodiments, full curing may be useful in some applications. For example, a balloon was 100% cured within the mold by an extended cure time that exceeded the amount required to ensure that 100% of the target property was achieved. Based on the chart shown in FIG. 34, a cure time of 5 minutes was used (i.e., over double the time required to achieve 90% of the target property). The samples showed higher average dog bone tensile forces (5.208 lbs vs. 4.874 lbs) with increased average elongation (1090% vs. 1078%); but the resistance to creep was drastically lower compared to samples processed to 90% of the target property in the mold.

According to embodiments, this enhancement showed decreased creep resistance relative to samples processed to 90% of the target property in the mold during an in vitro study in an accelerated in vitro test environment utilizing an acetone bath (average time to failure dropped from 41.54 hours in 90% mold-cured units to 17.63 hours based 100% mold-cured units). Based on the test data, the extended curing samples have potential application in acute or low creep (with a higher tensile force requirements) application.

Those skilled in the art will appreciate that embodiments and features of embodiments disclosed herein are combinable to create synergistic benefits.

This application incorporates by reference: U.S. Pat. Pub. No. 2007/0100367, published May 3, 2007; U.S. Pat. Pub. No. 2007/0100368, published May 3, 2007; U.S. Pat. Pub. No. 2007/0100369, published May 3, 2007; U.S. Pat. Pub. No. 2007/0149994, published Jun. 28, 2007; U.S. Pat. Pub. No. 2008/0243071, published Oct. 2, 2008; U.S. Pat. Pub. No. 2008/0319471, published Dec. 25, 2008; U.S. Pat. Pub. No. 2005/0159769, published Jul. 21, 2005; U.S. Pat. Pub. No. 2009/0048624, published Feb. 19, 2009; WIPO Pub. No. WO 2007/053556, published Oct. 5, 2007; WIPO Pub. No. WO 2007/053707, published Oct. 5, 2007; WIPO Pub. No. WO 2007/053706, published Oct. 5, 2007; and WIPO Pub. No. WO 2007/075810, published May 7, 2007; each as if fully set forth herein in its entirety.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A process for manufacturing a balloon of an intragastric device, the process comprising:
    subjecting materials for the balloon to a heated environment, wherein a fraction of a target property for the balloon is achieved by partial cross-linking due to the heated environment, and wherein the materials for the balloon are elastomeric materials;
    removing the balloon from the heated environment, wherein additional cross-linking is achieved and driven by residual heat retained from the heated environment; and
    subjecting the balloon to radiation-based sterilization, wherein about 100% of the target property is achieved.

2. The process of claim 1, wherein the target property is resistance to failure when subjected to a chemical stress.

3. The process of claim 1, wherein the target property is resistance to failure when subjected to a mechanical stress.

4. The process of claim 3, wherein the mechanical stress is torque.

5. The process of claim 3, wherein the mechanical stress is elongation.

6. The process of claim 1, wherein the target property is tensile strength.

7. The process of claim 1, wherein the target property is resistance to ingress and egress across walls of the balloon.

8. The process of claim 1, wherein the materials for the balloon are silicone-based.

9. The process of claim 1, wherein the radiation-based sterilization is gamma sterilization.

10. The process of claim 1 wherein the fraction is between about 85% and about 95% of the target property.

* * * * *

UNITED STATES PATENT AND TRADEMARK OFFICE
CERTIFICATE OF CORRECTION

PATENT NO.         : 8,683,881 B2
APPLICATION NO.    : 12/753751
DATED              : April 1, 2014
INVENTOR(S)        : Outhit Bouasaysy et al.

It is certified that error appears in the above-identified patent and that said Letters Patent is hereby corrected as shown below:

On Title Page 2, in column 2, Item (56), under "Other Publications", line 5, delete "Applicaton" and insert -- Application --, therefor.

On Title Page 3, in column 2, Item (56), under "Other Publications", line 14, delete "Ballon" and insert -- Balloon --, therefor.

Signed and Sealed this
Twenty-second Day of July, 2014

Michelle K. Lee
*Deputy Director of the United States Patent and Trademark Office*